(12) United States Patent
Piccirillo

(10) Patent No.: US 8,986,379 B2
(45) Date of Patent: Mar. 24, 2015

(54) GRAFT INTRODUCER

(71) Applicant: DePuy Mitek, LLC, Raynham, MA (US)

(72) Inventor: Justin M. Piccirillo, Uxbridge, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 13/799,527

(22) Filed: Mar. 13, 2013

(65) Prior Publication Data

US 2013/0274878 A1    Oct. 17, 2013

Related U.S. Application Data

(62) Division of application No. 13/247,180, filed on Sep. 28, 2011, now Pat. No. 8,556,970.

(51) Int. Cl.
*A61F 2/08* (2006.01)

(52) U.S. Cl.
CPC ............. *A61F 2/0811* (2013.01); *A61F 2/0805* (2013.01)
USPC ....................................................... 623/13.14

(58) Field of Classification Search
USPC .............................. 623/13.11–13.17; 606/232
See application file for complete search history.

(56) References Cited

U.S. PATENT DOCUMENTS

| | | | | |
|---|---|---|---|---|
| 5,266,075 A * | 11/1993 | Clark et al. | ................... | 606/138 |
| 5,601,562 A | 2/1997 | Wolf | | |
| 6,716,224 B2 | 4/2004 | Singhatat | | |
| 6,818,020 B2 * | 11/2004 | Sun et al. | ................... | 623/23.58 |
| 7,341,592 B1 | 3/2008 | Walters | | |
| 7,458,975 B2 * | 12/2008 | May et al. | ....................... | 606/53 |
| 7,572,283 B1 * | 8/2009 | Meridew | ....................... | 606/321 |
| 2004/0230194 A1 | 11/2004 | Urbanski | | |

FOREIGN PATENT DOCUMENTS

WO  WO 2010121271 A1  10/2010
WO  WO 2011041783 A1 *  4/2011

* cited by examiner

*Primary Examiner* — Suzette J Gherbi

(57) ABSTRACT

An instrument for placing a graft into a bone tunnel comprises an elongated shaft having a forked distal end comprising a pair of tines. A suture spans a space defined between the tines whereby the graft may be positioned between the tines and against the suture so as to be manipulated into the bone tunnel. The tendon folds about the suture, the suture having a releasable tension such that the instrument can be removed from the bone, leaving the tendon behind without the tendon hanging up on the suture.

12 Claims, 7 Drawing Sheets

GRAFT INTRODUCER

CROSS REFERENCE TO RELATED APPLICATIONS

This application is a divisional application of U.S. patent application Ser. No. 13/247,180, entitled GRAFT INTRODUCER, filed Sep. 28, 2011, which is incorporated herein by reference.

BACKGROUND

This application relates to tissue manipulation instruments, and more particularly to instruments for implantation of graft tissue into a bone hole.

In certain surgical procedures, such as tenodesis, a graft tissue is attached to a bone. For instance, in tenodesis a biceps tendon is detached from its attachment to the glenoid and is reattached to the humerus. In one popular method of reattachment a bone tunnel is created on the humerus and the detached tendon is pushed into the tunnel and then held in place via an interference bone screw implanted into the tunnel. Positioning the tendon in the tunnel can be tricky.

In one method, the graft tissue is externalized from the patient and whip stitched to make a stiff construct at the termination of the tissue. The stiff construct may be pushed directly into tunnel using graspers or the like. A length of suture at the distal portion of the whip stitch may be used to pull the graft tissue into the tunnel. It is desirable in many cases, however, to perform the entire operation with the graft tissue internalized within the patient. Thus, producing the whip stitch is difficult for the surgeon.

In another method, the graft tissue is folded near the location of tunnel and pushed into the tunnel at the fold. When using instrumentation of prior art, the graft tissue has a natural tendency to compress against the instrument. Should the frictional contact between the graft tissue and instrument be greater than the frictional contact between the graft tissue and tunnel, it is likely that the tissue will move from its desired position as the instrument is retracted from the tunnel.

SUMMARY OF THE INVENTION

The present invention overcomes these and other limitations of the prior art in a simple and elegant design.

An instrument according to the present invention provides for implanting a graft into a bone hole. The instrument comprises an elongated handle having a forked distal termination having a first tine and a second tine defining a space therebetween. A flexible member spans the space between the first tine and the second tine so that the graft can be received within the space against the flexible member and thereby manipulated into the bone hole.

Preferably, the first tine comprises an open ended first notch at its distal end, the flexible member being received within the first notch. Preferably, the flexible member having a first section between the first tine and second tine, and a second section extending from the first notch proximally along the handle where it preferably, is releasably attached to the handle so that a user can release the flexible member from the handle to relax tension in the flexible member. Preferably, the second tine comprises an open ended second notch with the flexible member being received in both the first notch and second notch and spanning the space therebetween.

In one aspect of the invention, one or both of the first tine and second tine are flexible, with the space between the first tine and second tine being adjustable by tension on the flexible member.

In one aspect of the invention, the handle is cannulated having a longitudinal cannulation opening to the space between the first tine and second tine. In one aspect of the invention, a guide wire is provided which is passable through the cannulation and which is adapted to be fixed into the bone hole whereby the instrument can be passed down to the bone hole over the guide wire.

Preferably, the first tine and second tine are curved about a central longitudinal axis of the instrument to accommodate to the bone hole.

Preferably, the instrument is provided sterile and packaged in a bacteria proof package.

A method according to the present invention provides for implanting a graft into a bone hole. The method comprises the steps of: positioning the graft between a first tine and a second tine at a distal end of a shaft of a surgical instrument and against a flexible member spanning a space defined between the first tine and second tine; manipulating the first and second tines with the graft therebetween into a bone tunnel; pushing the graft via the flexible member into the bone tunnel; and releasing tension in the flexible member to allow its movement relative to at least one of the first tine and second tine and removing the first and second tines from the bone tunnel, leaving the graft positioned therein.

Preferably, the graft is folded upon itself over the flexible member.

In one aspect of the invention, the flexible member is received in an open distally facing notch on the first tine. In one aspect of the invention, the step of releasing tension on the flexible member includes allowing it to fall outwardly of an open distally facing notch on the first tine.

In one aspect of the invention, at least one of the first tine and second tines are flexible a distance between them is controlled via tension on the flexible member.

In an aspect of the invention, the first tine and second tines are directed toward the bone tunnel by passing a guide wire leading from the bone tunnel through a cannulation through the shaft. After the graft has been positioned in the bone tunnel an anchor can be passed into the tunnel to fix the graft therein, preferably by passing the anchor over the guide wire.

DETAILED DESCRIPTION

Figure 1:
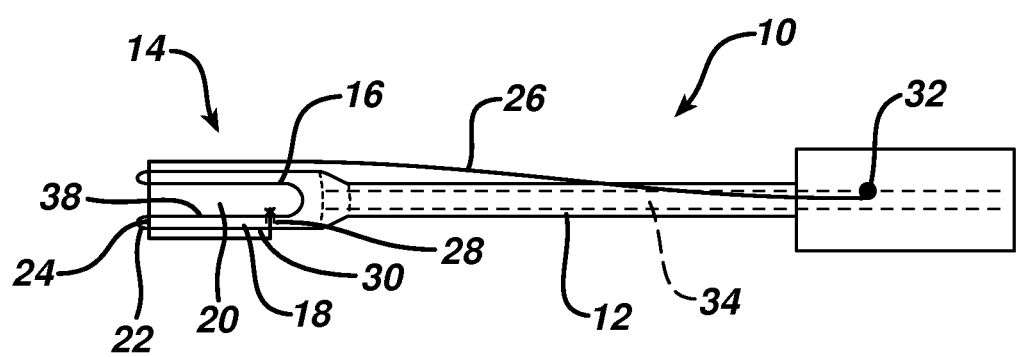
FIG. 1 is a side elevation view of a graft implantation tool according to the present invention.

FIG. 1 depicts a graft implantation tool 10 according to the present invention. It comprises an elongated cannulated shaft 12 with a forked distal end 14. The distal end 14 comprises a first tine 16 and second tine 18 defining a space 20 therebetween. Each of the tines 16 and 18 has a distal terminal end 22 with a distal terminal notch 24. A length of suture 26 or other flexible material with suitable tensile strength spans the space 20 between the notches 24. It has a first end 28 affixed to the shaft 12 where the second tine 18 meets the shaft 12. From there it extends down along an exterior surface 30 of the second tine 18 enters the second tine notch 24, spans the space 20, enters the first tine notch 24 and then extends up the shaft 14 where it is secured in a suture retainer 32, which is shown for illustrative purposes as a simple cleat but any suitable retention can be employed as will be appreciated by those of skill in the art.

A cannulation 34 extends axially through the shaft 12 and opens into the space 20 between the tines 16 and 18. The cannulation 34 is wide enough to pass an interference anchor 36 (see FIG. 2). The tines 16 and 18 are curved on their exterior surfaces 30 and interior surfaces 38 to fit snugly into a bone tunnel (not shown in FIG. 1) and to pass the anchor 36. One or both of the tines 16 and 18 can be flexible with their spacing being controlled by tension in the suture 26 spanning the space 20. In such event their relaxed position is preferably slightly spread from parallel as they extend distally. This allows a more open presentation to allow easier loading of a graft (not shown in FIG. 1) into the space 20.

Figure 2:
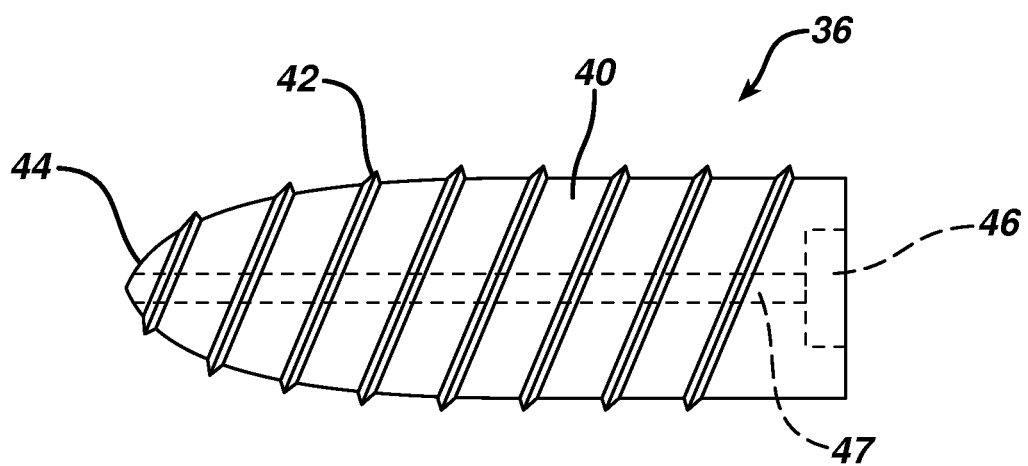
FIG. 2 is a side elevation view of a graft anchor for use with the tool of FIG. 1.

Turning also now to FIG. 2, the anchor 36 comprises an elongated body 40 having exterior threads 42, a narrow distal tip 44, a proximal tool recess 46, such as for receipt of a hex driver, and an axial cannulation 47 for passage of a guide wire (not shown in FIGS. 1 and 2). Other configurations can be employed as will be appreciated by those of skill in the art. One suitable anchor is the MILAGRO interference screw available from DePuy Mitek, Inc. of Raynham, Mass.

The tool 10 can be fabricated from any biocompatible materials or combinations thereof providing adequate strength for constructing the cannulated shaft 12 and having adequate elastic properties to provide the flexibility of one or both tines 16, 18 to accommodate variations in the distance across the space 20. Metallic materials that can be used to manufacture the instrument of the present invention include stainless steel, titanium, alloys of nickel and titanium, or other biocompatible metallic materials. It can also be formed of polyethylene, polypropylene, PEEK, or other biocompatible non-absorbable polymers.

Figure 3:
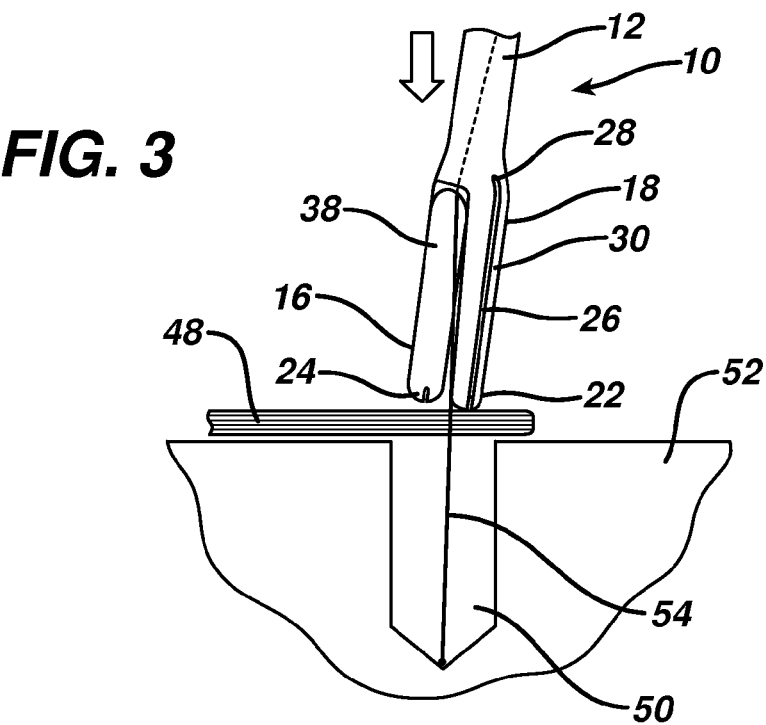
FIG. 3 is a side elevation view of the tool of FIG. 1 shown adjacent a bone tunnel and a graft ready for implantation into the tunnel.
Figure 4:
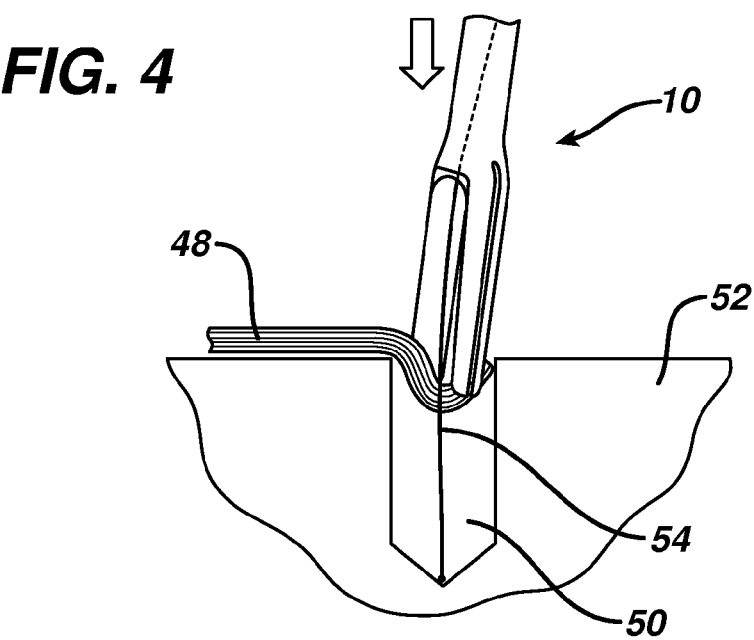
FIG. 4 is a side elevation view of the tool of FIG. 1 shown initially capturing the graft and entering the tunnel.
Figure 5:
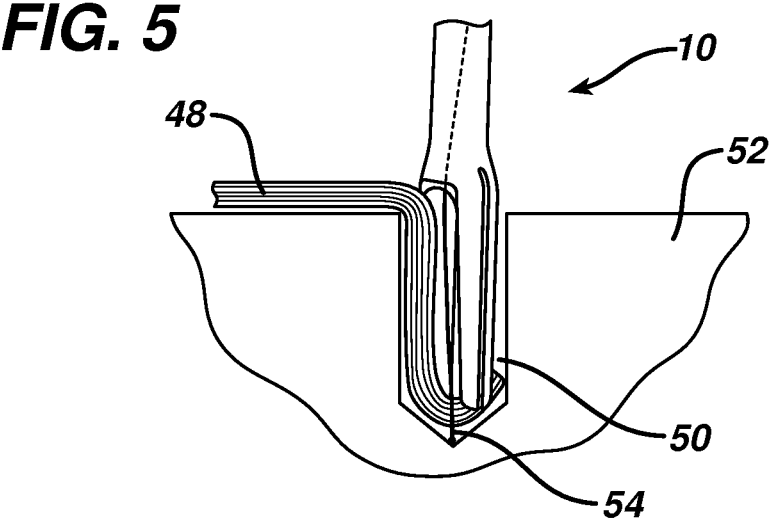
FIG. 5 is a side elevation view of the tool of FIG. 1 shown fully inserted into the tunnel.
Figure 6:
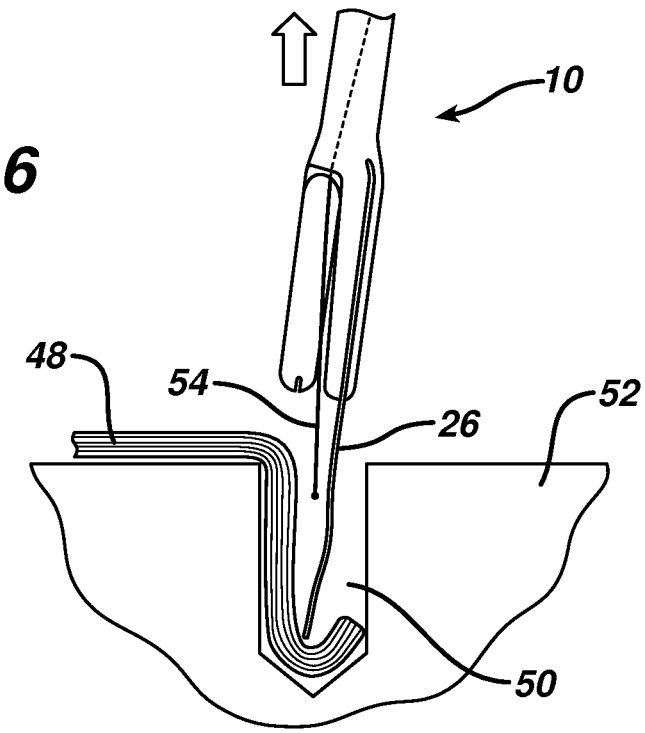
FIG. 6 is a side elevation view of the tool of FIG. 1 shown retracting from the tunnel leaving the graft in the tunnel.
Figure 7:
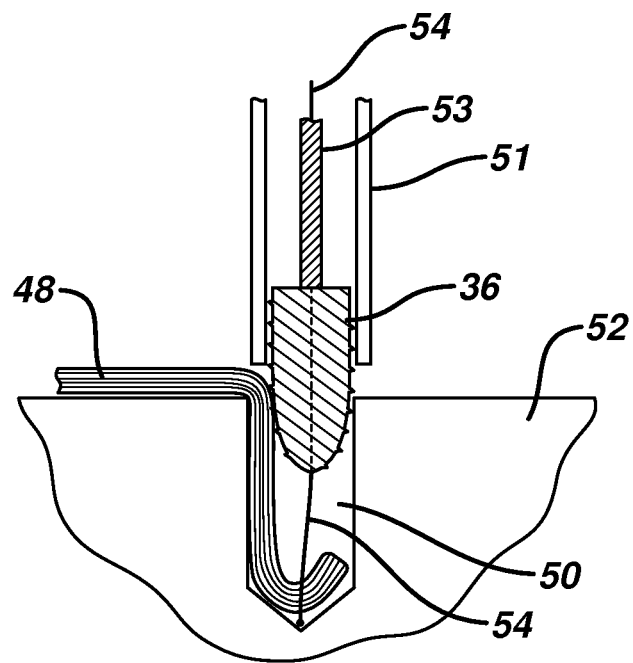
FIG. 7 is a side elevation view of the tool of FIG. 1 oriented to show the graft entering the tunnel from the rear of this view and an anchor being implanted into the tunnel.
Figure 8:
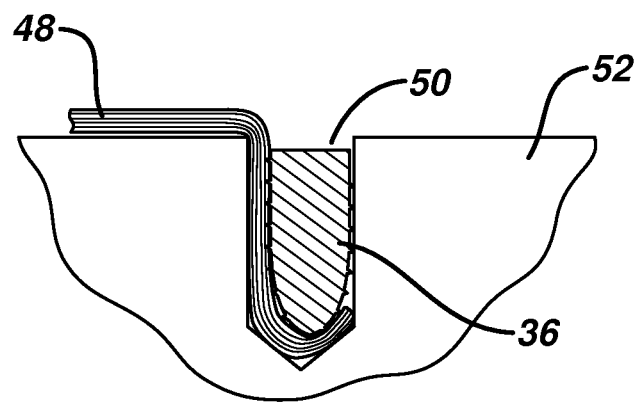
FIG. 8 is a side elevation view of the tunnel and graft of FIG. 7 oriented to show the graft entering the tunnel from the left side and illustrating a completed implantation of the graft.

Turning also to FIGS. 3 to 6, use of the tool 10 will now be described. FIG. 3 shows a biceps tendon 48 which has been removed from its placement on the glenoid (not shown) and is placed adjacent to a bone tunnel 50 which has been prepared in a humerus bone 52. A guide wire 54 extends from the tunnel 50. Options for creation of the bone tunnel 50 and placement of the guide wire 54 will be apparent to those of skill in the art. The tool 10 has been passed down over the guide wire 54 and is positioned adjacent to the tunnel 50. The tendon 48 is positioned over the tunnel 50 with the suture 26 orthogonal to the tendon 48. As the tines 16 and 18 are pressed into the tunnel 50 (FIG. 4) the tendon 48 is received between the tines 16 and 18 and caught upon the suture 26 causing the tendon 48 to fold upon itself. The tendon 48 is then pressed down into the bottom of the tunnel 50 as illustrated in FIG. 5. At this time the suture 26 is released from the suture retainer 32 releasing tension in the suture 26 and allowing removal of the tines 16 and 18 without the suture hanging up on the tendon 48 and affecting its implantation in the tunnel 50 as illustrated in FIG. 6. The anchor 36 can then be implanted, preferably over the guide wire 54 employing techniques as may be known or become known to those of skill in the art. For instance, FIG. 7 shows the anchor 36 being passed down a cannula 51 via a cannulated driver 53 and being threaded into the tunnel 50 to trap the tendon 48 therein. FIG. 8 illustrates the completed repair.

Figure 9:
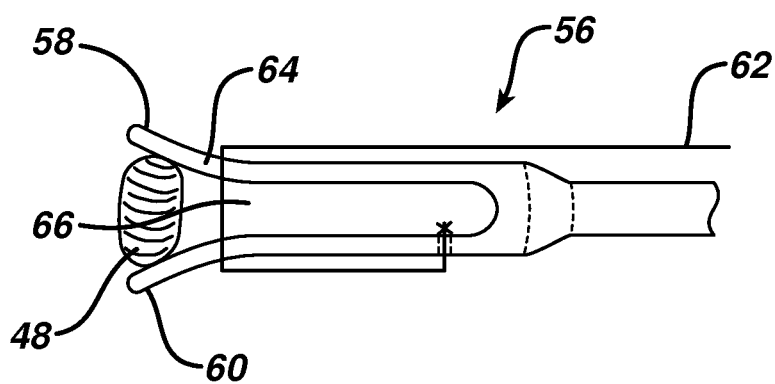
FIG. 9 is a side elevation view of an alternative embodiment of a graft implantation tool according to the present invention showing flexible tines in a relaxed state.
Figure 10:
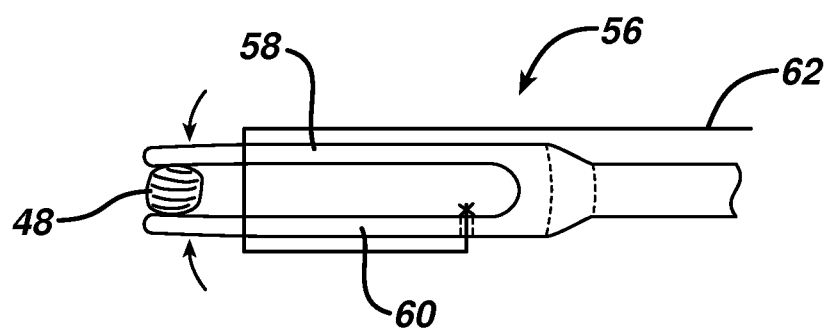
FIG. 10 is a side elevation view of the tool of FIG. 9 showing the tines in a collapsed state.

FIGS. 9 and 10 illustrate an alternative embodiment of a graft implantation tool 56 according to the present invention. It has flexible first and second tines 58 and 60, respectively, and a suture 62 passing from the second tine 60 through a distal notch 64 therein across a space 66 between the tines 58 and 60, through a distal notch 64 in the first tine 58. Under slack tension in the suture 62 distal ends 68 of the tines 58 and 60 spread open allowing easy entry of a graft 66 into the space 66. Tension on the suture 62 causes the tines 58 and 60 to collapse inwardly toward each other grasping the graft 66. The narrowing of the tine spacing may also ease its entry into a bone tunnel.

Figure 11A:
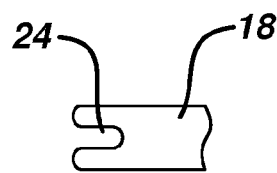
FIG. 11A is a side elevation view of a tine of FIG. 1 showing a suture capture notch.
Figure 11B:
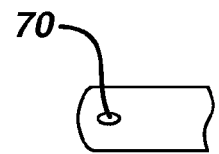
FIG. 11B is a side elevation view of a tine of an alternative embodiment of a graft implantation tool according to the present invention showing a suture capture hole.
Figure 11C:
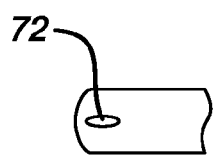
FIG. 11C is a side elevation view of a tine of an alternative embodiment of a graft implantation tool according to the present invention showing an elongated suture capture hole.
Figure 11D:
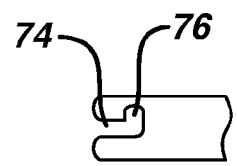
FIG. 11D is a side elevation view of a tine of an alternative embodiment of a graft implantation tool according to the present invention showing an alternative suture capture notch.
Figure 11E:
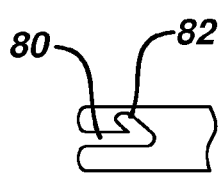
FIG. 11E is a side elevation view of a tine of an alternative embodiment of a graft implantation tool according to the present invention.
Figure 11F:
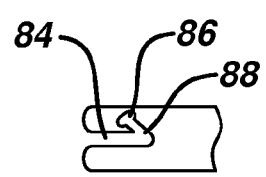
FIG. 11F is a side elevation view of a tine of an alternative embodiment of a graft implantation tool according to the present invention.
Figure 11G:
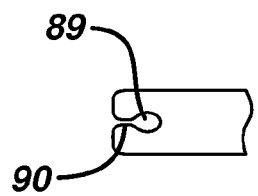
FIG. 11G is a side elevation view of a tine of an alternative embodiment of a graft implantation tool according to the present invention.
Figure 11H:
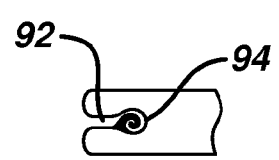
FIG. 11H is a side elevation view of a tine of an alternative embodiment of a graft implantation tool according to the present invention.

Although shown with tines 16 and 18 which are axially aligned with the shaft 12 they could be angled with respect to the shaft 12. Also the shaft could be curved. Various depths of the notches 24 into the tines 16 and 18 may be employed for positioning the graft tendon 48 at different axial positions along the tines 16 and 18. The tension on the suture 26 can also affect such placement with a bit of slack in it between the notches 24 allowing the suture 26 to bow proximally as the tendon 48 is engaged. Turning also now to FIGS. 11 A to H, the axial notch 24 as disclosed in FIG. 1 and FIG. 11A is preferred in the first tine 16 for easy release of the suture 26 from the tendon 48 after its implantation without the suture 26 catching on tendon 48 or the tine 16. Other designs may enhance temporary holding of the suture 26 so that it does not fall out of place. For instance a closed circular hole 70, elongated hole 72 or elongated notch 74 with a capture leg 76 or notch 80 and more aggressive capture leg 82 may be substituted especially in the second tine 18. A notch 84 having an expanded capture leg 86 and a restriction 88 leading into the capture leg 86 allows suture to slip in easily but not slip back out. A notch 89 with a restriction 90 provides some measure of capture but still allows the suture to be extracted from the notch 89 if desired. A notch 92 can be provided with a tortuous path such as in inward spiral 94. These designs limit suture 26 from falling out of the notch inadvertently yet still allow free sliding of the suture 26 therethrough so that it will not catch on the tendon 48 as the tines 16 and 18 are removed from the tunnel 50.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An instrument for implanting a graft into a bone hole, the instrument comprising:
    an elongated handle having a forked distal termination;
    the distal termination comprising a first tine and a second tine defining a space therebetween;
    a flexible member spanning the space between the first tine and the second tine with the graft received within the space against the flexible member with the flexible member passing proximal of the graft whereby to facilitate manipulation of the graft into the bone hole.

2. An instrument according to claim 1 wherein the first tine comprises an open ended first notch at its distal end, the flexible member being received within the first notch.

3. An instrument according to claim 2 wherein the flexible member having a first section between the first tine and second tine, and a second section extending from the first notch proximally along the handle.

4. An instrument according to claim 3 wherein the second section is releasably attached to the handle wherein a user can release the flexible member from the handle to relax tension in the flexible member.

5. An instrument according to claim 2 and further comprising the second tine comprising an open ended second notch, the flexible member being received in both the first notch and second notch and spanning the space therebetween.

6. An instrument for implanting a graft into a bone hole, the instrument comprising:
    an elongated handle having a forked distal termination;
    the distal termination comprising a first tine and a second tine defining a space therebetween;
    a flexible member spanning the space between the first tine and the second tine whereby the graft can be received within the space against the flexible member and thereby manipulated into the bone hole; and
    wherein at least one of the first tine and second tine are flexible, the space between the first tine and second tine being adjustable by tension on the flexible member.

7. An instrument according to claim 2 wherein the handle is cannulated having a longitudinal cannulation opening to the space between the first tine and second tine.

8. An instrument according to claim 7 and further comprising a guide wire passable through the cannulation and adapted to be fixed into the bone hole whereby the instrument can be passed down to the bone hole over the guide wire.

9. An instrument according to claim 8 wherein the first tine and second tine are curved about a central longitudinal axis of the instrument to accommodate to the bone hole.

10. An instrument according to claim 1 which is sterile and packaged in a bacteria proof package.

11. An instrument according to claim 1 wherein the flexible member has a first end attached to the instrument at the distal termination.

12. An instrument according to claim 1 wherein the graft is folded over the flexible member.

* * * * *